United States Patent [19]

Vachy et al.

[11] Patent Number: 6,153,226

[45] Date of Patent: Nov. 28, 2000

[54] THERAPEUTIC COMPOSITION CONTAINING A PHENOL COMPOUND AND PROPOLIS, WHICH IS USEFUL AGAINST LIPID CAPSID VIRUSES, ESPECIALLY HERPES VIRUSES

[75] Inventors: Robert Vachy, Paris; Françoise Sauvager, Chantepie; Maryvonne Amoros, Pace, all of France

[73] Assignee: Fileco, Paris, France

[21] Appl. No.: 07/930,411

[22] PCT Filed: Mar. 8, 1991

[86] PCT No.: PCT/FR91/00186

§ 371 Date: Oct. 11, 1992

§ 102(e) Date: Oct. 11, 1992

[87] PCT Pub. No.: WO91/13626

PCT Pub. Date: Sep. 19, 1991

[30] Foreign Application Priority Data

Mar. 12, 1990 [FR] France ................................. 90 03093
Mar. 8, 1991 [WO] WIPO ..................... PCT/FR91/00186

[51] Int. Cl.[7] .......................... A61K 35/64; A61K 31/05
[52] U.S. Cl. ............................................. 424/539; 514/731
[58] Field of Search .............................. 424/539; 514/731

[56] References Cited

PUBLICATIONS

Weuffen et al 73 CA: 128140a 1970.
Glinnik et al 95 CA: 144148p 1981.
Sheuvhenko et al 82 CA: 68322e 1975.
Meresta et al 109 CA: 351198s 1988.
Snipes et al 92 CA: 221x 1980.
Vachy 98 CA: 204426b 1983.
Wright 72 CA: 75997a 1970.
Prakash et al 93 CA: 199103j 1980.
Popescu et al 103 CA 220838q 1985.
Anan'ev et al 105 CA: 54144e 1986.
Thiel et al 84 CA: 160055j 1976.
Knight et al 88 CA: 182572k 1978.
Kane et al 109 CA: 47853q 1988.
Database WPI (L)/Derwent, No. 83–762896, & RO, A, 81340 (Colentina Spitalul) 1985.
Chemical Abstracts, vol. 103, No. 26, Dec. 30 1985, (Columbus, OH, US), see p. 359, abstract 220838q, & RO, A 86003 Institutul De Medicina & Farmacie) Jan. 30, 1985.
Chemical Abstracts, vol. 83, No. 17, Oct. 27, 1975, (Columbus, OH, US), A.I. Tikhonov et al.: Phisiochemical and microbiological properties and quantitative determinations of water–soluble.

*Primary Examiner*—Marianne M. Cintins
*Attorney, Agent, or Firm*—Ostrolenk, Faber, Gerb & Soffen, LLP

[57] ABSTRACT

The present invention concerns a novel therapeutic compositions comprising a phenol component and propolis which is useful in combating lipidic capside viruses, which contains (1) 100 to 650 parts by weight of phenol component for (ii) one part by weight of propolis. This novel composition is especially useful in the treatment of herpes, especially the diseases caused by the virus strains $HSV_1$, $HSV_2$ $HSV_1R$.

11 Claims, No Drawings

THERAPEUTIC COMPOSITION CONTAINING A PHENOL COMPOUND AND PROPOLIS, WHICH IS USEFUL AGAINST LIPID CAPSID VIRUSES, ESPECIALLY HERPES VIRUSES

FIELD OF THE INVENTION

The present invention relates to a novel therapeutic composition containing a phenol component and propolis. This composition is userful as an antiviral agent, in general against lipid capsid viruses (abbreviated to LCV's) and in particular against herpes viruses and their analogs which form part of the LCV group.

PRIOR ART

It is known that phenols have already been recommended in therapeutics as anti-infective agents on account of their bacteriostatic or mycostatic properties.

Among these phenols, it is known, in particular from French patent FR-B-2 507 891, the article by W. SNIPES et al., Sciences, 187, pages 64–65 (1975), and the articles by W. SNIPES et al. entitled "Hydrophobic Alcohols and Di-tert-butyl Phenols as Antiviral Agents" and published in the work "Symposium on the Pharmacological Effects of Lipids", pages 63–73, The American Oil Chemists' Society, Champaign, Illinois (1978), that the BHT's of formula I below, namely the 4-alkyl-2,6-di-t-butylphenols in which the alkyl group in the 4-position contains a linear hydrocarbon chain of 1 to 12 carbon atoms, have inhibitory and/or virucidal effects on LCV's and especially herpes viruses. According to the second article by W. SNIPES et al. cited above, it is known that the antiherpetic activity depends on the nature of the 4-alkyl group of the BHT and that the BHT which has an n-butyl radical in the 4-position is virtually the only one active against $HSV_2$.

It is further known that propolis is a gummy substance recovered from beehives. More precisely, it is a substance which the bees collect from certain plants, especially the scales of poplar and alder buds, amass and use for filling in cracks in the beehives, fixing the honeycombs and glazing the walls. In the field of apiculture, propolis is known to be the antibiotic or disinfectant in the beehive, preventing bacteria and molds from proliferating.

Crude propolis generally contains resins and balsamic substances (approximately 55–50% by weight), beeswax (approximately 30–35% by weight), ethereal oils (approximately 10% by weight) and pollens (approximately 5% by weight); see especially EP-A-0 061 508 (page 2, lines 1–28), EP-A-0 109 993 (page 1, lines 24–26) and E. M. SCHNEIDEWIND et al., Die Pharmazie 34, 103 (1978).

The antiviral properties of propolis extracted from beehives and purified, against herpes viruses (especially $HSV_1$ and $HSV_2$) and influenza viruses (especially $IV_A$), are known especially from EP-A-0 061 508 (page 3, lines 6–7) and EP-A-0 109 993 (page 2, lines 3–8; page 10, lines 7–11; and page 11, lines 1–4) cited above, on the other hand, and EP-A-0 310 757 (page 3, lines 31–32), on the other.

Furthermore, a technique for the treatment of viral infections is known from abstract n° 83-762896 in DATABASE WPI/L of Derwent Publications Ltd, which relates to document R0-A-81 340, according to which technique (a) an alcoholic solution of propolis is administered orally and, simultaneously, (b) the locally affected areas are coated with an alcoholic propolis composition which may contain a phenol component (in the case in question, salicyclic acid as an anti-inflammatory agent) and/or vitamins; also, an antiherpes composition comprising propolis (one part by weight), phenol (0.5 part by weight) and menthol (one part by weight) is known from Chemical Abstracts CA 103, 220838q, which relates to document R0-A-86 003.

Now, it so happens that these last two documents neither describe nor suggest the synergistic composition of the invention, in which the weight ratio phenol component/propolis is between 100/1 and 650/1.

AIM OF THE INVENTION

According to the invention, a novel technical solution is recommended which uses an antiviral composition comprising a synergistic mixture of a phenol component and propolis in association.

This novel technical solution is advantageous in the sense that it makes it possible especially to reduce the practical doses previously recommended in the antiviral indications for the phenol component and propolis.

According to another feature of the invention, a method of preparing said composition is proposed.

SUBJECT OF THE INVENTION

It has now been found, surprisingly, that particular mixtures containing a phenol component and propolis have synergistic properties.

The therapeutic composition recommended according to the invention, which comprises a phenol component and propolis and which is useful as an antiviral agent against LCV's, contains (i) from 100 to 650 parts by weight of phenol component to (ii) one part by weight of propolis.

The method of preparation according to the invention consists in mixing the phenol component with the propolis in a weight ratio phenol component/propolis of 100/1 to 650/1.

ABBREVIATIONS

For convenience, the following abbreviations have been used in the present description:

BHT=2,6-di-t-butylphenol compound of formula I below [the letters BHT originate historically from the expression "butylated hydroxy-toluene"]

BpA=bisphenol A

BpB=bisphenol B

Bzp=2-benzylphenol compound of formula II below

Cp=phenol component

EBV=Epstein Barr virus

Et=ethyl

EtO=ethoxy

HG1=2,6-di-t-butylparacresol (i.e. BHT of formula I in which R is methyl)

HG4=2,6-di-t-butyl-4-butylphenol (i.e. BHT of formula I in which R is n-butyl) HGt4=2,4,6-tri-t-butylphenol (i.e. BHT of formula I in which R is t-butyl)

HGt5=2,6-di-t-butyl-4-(2,2-dimethylpropyl)phenol [i.e. BHT of formula I in which R is $CH_2C(CH_3)_3$]

HG6=2,6-di-t-butyl-4-hexylphenol (i.e. BHT of formula I in which R is n-hexyl)

HGt8=2,6-di-t-butyl-4-(1,1,3,3-tetramethylbutyl)phenol [i.e. BHT of formula I in which R is $C(CH_3)_2$—$CH_2$—$C(CH_3)_3$]

HSV₁=herpes simplex virus type 1

HSV₂=herpes simplex virus type 2

HSV₁R=herpes simplex virus type 1 resistant to acyclover [a reference antiviral substance of the structural formula 2-amino-1,8-dihydro-9-[(2-hydroxyethoxy) methyl]-6H-purin-6-one]

IV$_A$=influenza virus type A

LCV=lipid capsid virus

Me=methyl

MeO=methoxy

Prp=propolis

R$_w$=weight ratio

RT=room temperature (15–20° C.)

TV=infectious titer of the virus sample

ZV=Zoster virus

DETAILED DESCRIPTION OF THE INVENTION

As indicated above, it is important from the synergy point of view for the therapeutic composition according to the invention to comprise the phenol component (Cp) and the propolis (Prp) in a weight ratio R$_w$=Cp/Prp) of between 100/1 and 650/1 and advantageously with an R$_w$ of between 135/1 and 560/1.

The phenol component (Cp) used according to the invention is a compound selected from phenols and mixtures thereof. The phenol component can be a mono- or polyhydroxylated compound comprising in its molecule at least one non-fused benzene ring, at least two fused benzene rings or at least three fused OH benzene rings, it being possible for one of these phenolic OH groups to be etherified, replaced with a carboxyl group or replaced with a group CHO.

The following may be mentioned in particular among the compounds covered by the definition of Cp: phenol, pyrocatechol, resorcinol, hydroquinone (or benzene-1,4-diol), benzene-1,2,4-triol, pyrogallol (or benzene-1,2,3-triol), phloroglucinol (or benzene-1,3,5-triol), gallic acid (or 3,4,5-trihydroxybenzoic acid), saligenol (or 2-hydroxybenzenemethanol), vanillin (or 4-hydroxy-3-methoxybenzaldehyde), vanillyl alcohol (or 4-hydroxy-3-methoxybenzenemethanol), vanillic acid (or 4-hydroxy-3-methoxybenzoic acid), vanillylmandelic acid (or 4-hydroxy-3-methoxymandelic acid), o-cresol, m-cresol, p-cresol, o-cresotic acid (or 2-hydroxy-3-methylbenzoic acid), m-cresotic acid (or 2-hydroxy-4-methylbenzoic acid), p-cresotic acid (or 2-hydroxy-5-methylbenzoic acid), guaiacol (or 2-methoxyphenol), eugenol (or 4-allylguaiacol), oreosol (or 2-methoxy-4-methylphenol), thymol (or 2-isopropyl-5-methylphenol), orcinol (or 5-methylbenzene-1,3-diol), p-anol [or 4-(prop-1-enyl) phenol], salicyclic acid (or 2-hydroxy-benzoic acid), chavicol [or 4-(prop-2-enyl) phenol], carvacrol [or 2-methyl-5-(1-methylethyl)phenol or iso-propyl-o-cresol], 4-t-butylphenol, butylparaben (or n-butyl 4-hydroxybenzoate), benzoresorcinol (or 2,4-dihydroxyphenyl phenyl methanone), bisphenol A [or 4,4'-(1-methylethylidene) bisphenol, abbreviated to BpA], bisphenol B [or 4,4'-(1-methylpropylidene)bisphenol, abbreviated to BpB], bis(2-hydroxy-4-methoxyphenyl) methanone, 1-naphthol, 2-naphthol, anthranol (or anthracen-9-ol), anthrarobin (or anthracene-1,2,10-triol), anthralin [or 1,8-dihydroxy-(10H)-anthracen-9-one], anthrarufin (or 1,5-dihydroxyanthracene-9,10-dione) and mixtures thereof.

The BHT's and Bsp's of formulae I and II, respectively, may also be mentioned among the Cp's which are suitable.

The BHT's are 2,6-di-t-butylphenol compounds of the formula

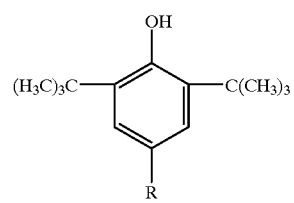

(I)

in which R is the hydrogen atom or a $C_1$–$C_{12}$ alkyl group with a linear or branched hydrocarbon chain.

The following in particular are covered by formula I: 2,6-di-t-butylparacresol (HG1), 2,6-di-t-butyl-4-butylphenol (HG4), 2,6-di-t-butyl-4-t-butylphenol (HGt4), 2,6-di-t-butyl-4-hexylphenol (HG6), 2,6-di-t-butyl-4-(1,1,3,3-tetramethylbutyl) phenol (HGt8) and mixtures thereof.

The Bzp's are 2-benzylphenol compounds of the formula

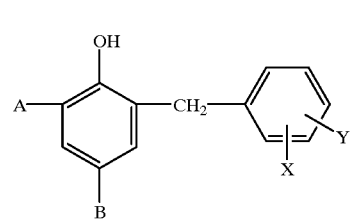

(II)

in which

X and Y independently of one another are each the hydrogen atom, a group OH, a group OMe or a group OEt, it being possible for X and Y, taken together, to be a 3,4-methylenedioxy radical, A is H or a radical $CH_2C_6H_3XY$, in which X and Y are defined as indicated above, and B is the hydrogen atom or a $C_1$–$C_{12}$ alkyl group with a linear or branched hydrocarbon chain.

The Cp compounds containing an unsaturated aliphatic side-chain, for example prop-1-enyl or prop-2-enyl, are used not by themselves but in association with at least one other Cp devoid of ethylenic or acetylenic unsaturation on a side-chain. In fact, the Cp compounds which do have an ethylenic or acetylenic unsaturation are liable to polymerize under the action of light. It is therefore of interest, according to the invention, to associate them with at least one other phenol having anti-UV properties so as to avoid any polymerization during storage.

The preferred phenol component according to the invention will be selected from BpA, pyrogallol, pyrocatechol, carvacrol, BHT's and mixtures thereof. The most valuable Cp compounds according to the invention are the BHT's and especially HG1, HGt4, HG4, HG6, HGt5 and HGt6.

The propolis component which forms part of the composition according to the invention will be a purified Prp, especially a Prp soluble in water or the customary organic solvents, which is obtained by treating crude Prp with an alcohol, such as MeOH or EtOH, or a water/alcohol mixture. The Prp's obtained by the methods described in DE-A-1 037 651, FR-A-2 256 764, FR-A-2 374 030, FR-A-2 594 336, EP-A-0 061 508, EP-A-0 109 993, EP-A-0 135 601 and EP-A-0 310 757, which take the form of white or light brown powders or granules, are particularly suitable for this purpose.

The therapeutic composition which is useful in the treatment of the viral diseases caused by the LCV's will comprise the Cp/Prp mixture with an $R_w$ of between 100/1 and 650/1, in association with one or more excipients appropriate for oral administration, administration by injection or local administration.

Such a composition will be particularly advantageous when used against herpes and diseases analogous to herpes. It has in fact been found that such a composition is particularly effective in the treatment of herpes simplex type 1 and type 2, especially the diseases caused by the $HSV_1$ and $HSV_1R$ strains, which are transmissible by contact between mucosa, on the one hand, and the diseases caused by the $HSV_2$ strains, which are sexually transmissible and include especially condyloma latum, on the other.

The antiviral composition according to the invention can be prepared by a method known per se. The recommended method consists in mixing the Cp component and Prp component in an appropriate aqueous or oily physiological medium at a temperature between RT and 75° C.

BEST MODE

The best mode of carrying out the invention consists in using a composition of BHT and Prp in which the BHT is 2,6-di-t-butylparacresol (HG1), 2,4,6-tri-t-butylphenol (HGt4), 2,6-di-t-butyl-4-n-hexylphenol (HG6) or 2,6-di-t-butyl-4-(1,1,3,3-tetramethylbutyl) phenol (HGt8), with a ratio of $R_w$ of between 135/1 and 680/1.

According to the invention, a novel therapeutic use is recommended, wherein a mixture comprising a phenol component and propolis in a weight ratio phenol component/propolis of between 100/1 and 650/1, and preferably of between 135/1 and 560/1, is used to obtain an antiviral drug for use in human or veterinary therapeutics against the diseases caused by lipid capsid viruses, especially the diseases caused by the following strains: (i) $HSV_1$, $HSV_2$ and $HSV_1R$, and (ii) $IV_A$, EBV and ZV.

Further advantages and characteristics of the invention will be understood more clearly from the following description of Comparative Experiments and Preparatory Examples. Of course, these data as a whole in no way imply a limitation but are given by way of illustration.

EXAMPLE 1

Comparative Experiments

The following are used: a culture medium containing HG1 at concentrations of 50 or 25 mg/ml and solutions of Prp at decreasing concentrations of 0.363 mg/ml, 0.272 mg/ml, 180 mg/ml, 136 mg/ml and 0.090 mg/ml. Equal volumes of said culture medium and said solutions are incubated in the presence of $HSV_1R$ for 1 h at 37° C., with shaking. After centrifugation, the infectious titers are determined in the usual manner by the so-called limiting dilution method and compared with control samples of $HSV_1R$ virus, control samples of propolis and control samples of HG1, incubated under the same conditions (it was necessary to prepare control samples of excipient since previous experiments had demonstrated the absence of an effect of the excipient on viruses, especially $HSV_1R$).

The method used to measure the interaction between Cp and Prp precisely was that described by R. F. SCHINAZI et al., Antimicrob. Agents Chemother., 22 (n° 3), pages 499–507 (1982) and reworked by J. C. POTTAGE, ibidem 30 (n° 2), pages 215–219 (1986), incorporating the following definitions:

$Y_a$=infectious titer in the presence of Prp/TV, $Y_b$=infectious titer in the presence of HG1/TV, $Y_{ab}$=infectious titer in the presence of Prp+HG1/TV, $Y_o=Y_a \times Y_b$.

If:

1°) $Y_{ab}<Y_o$, the interaction is synergistic,

2°) $Y_{ab}>Y_o$ but < the more active compound by itself, the interaction is in this case a subadditive reaction, 3°) $Y_{ab}$>the less active compound by itself, the interaction is antagonistic, and 4°) $Y_{ab}$>the more active compound but < the less active compound, the interaction is then called interference.

To simplify the calculations, the infectious titers found in the experiments on HG1/Prp associations and the control experiments were expressed as their decimal logarithm. The results obtained have been collated in Table I below.

The results in Table I show that:

at the highest concentrations used (Prp 0.363 mg/ml and HG1 50 mg/ml), it is not possible to observe an interaction since propolis by itself is virucidal at this dose, at a Prp concentration of 0.272 mg/ml, only an interference effect with HG1 is observed, on the other hand, at the low Prp concentrations (0.090 to 0.180 mg/ml), there is a synergy with HG1 occurring at a concentration of 25 or 50 mg/ml.

In the case in question, there is a synergy when the ratio $R_w$=HG1/Prp is between 135/1 and 560/1.

TABLE I

STUDY OF THE ASSOCIATION Prp/HG1 ON THE INFECTIOUS TITER OF $HSV_1R$

| TV | Prp titer | HG1 titer | Prp + HG1 experiments | $Y_a$ | $Y_b$ | $Y_{ab}$ | $Y_0$ | Interaction |
|---|---|---|---|---|---|---|---|---|
| 4.5 | 3.5 (a) | 2 (f) | 0.5 | 0.77 | 0.44 | 0.11 | 0.33 | synergy |
| 4.5 | 4.5 (a) | 3 (g) | 2.5 | 1 | 0.66 | 0.55 | 0.66 | synergy |
| 5.0 | 4.0 (a) | 2 (g) | 0 | 0.8 | 0.4 | 0 | 0.32 | synergy |
| 4.5 | 2.5 (b) | 2 (f) | 0 | 0.55 | 0.44 | 0 | 0.24 | synergy |
| 4.0 | 1.0 (c) | 1 (f) | 0 | 0.25 | 0.25 | 0 | 0.06 | synergy |
| 4.5 | 1.5 (c) | 2 (f) | 0 | 0.33 | 0.44 | 0 | 0.14 | synergy |
| 4.5 | 3.5 (c) | 3 (g) | 2 | 0.77 | 0.66 | 0.44 | 0.50 | synergy |
| 5.0 | 3.0 (c) | 2 (g) | 1 | 0.6 | 0.4 | 0.2 | 0.24 | synergy |
| 4.0 | 0 (d) | 2 (f) | 0.5 | 0 | 0.5 | 0.12 | 0 | interference |

TABLE I-continued STUDY OF THE ASSOCIATION Prp/HG1 ON THE INFECTIOUS TITER OF $HSV_1R$

| TV | Prp titer | HG1 titer | Prp + HG1 experiments | $Y_a$ | $Y_b$ | $Y_{ab}$ | $Y_0$ | Interaction |
|---|---|---|---|---|---|---|---|---|
| 5.0 | 1.0 (d) | 2 (g) | 1.0 | 0.2 | 0.4 | 0.25 | 0.08 | interference |
| 4.0 | 0 (e) | 2 (f) | 0 | 0 | 0.5 | 0 | 0 | (h) |

Notes
(a) Prp at a concentration of 0.090 mg/ml
(h) Prp at a concentration of 0.138 mg/ml
(c) Prp at a concentration of 0.180 mg/ml
(d) Prp at a concentration of 0.272 mg/ml
(e) Prp at a concentration of 0.363 mg/ml
(f) HG1 at a concentration of 50 mg/ml
(g) HG1 at a concentration of 25 mg/ml
(h) excessively high dose of Prp

EXAMPLE 2

Formulation

A mixture of 59 g of white petrolatum, 2.99 g of sorbitan sesquioleate and 3 g of glycerol monooleate is heated to 70–75° C. Heating is stopped when the mixture has become homogeneous, after which 5 g of HG6 and then 0.01 g of propolis are added, with stirring. 30 g of water are then added at a temperature below or equal to 65° C. and stirring is continued until the mixture has cooled to RT. It is homogenized to give an ointment consisting of a water-in-oil emulsion, which can be used as an eye lotion.

EXAMPLE 3

Formulation 56.98 g of white petrolatum, 3.5 g of sorbitan sesquioleate and 3.5 g of glycerol monooleate are mixed at 70–75° C. When the mixture has become homogeneous, heating is stopped and 7 g of HG1 are added. Mixing is resumed and a mixture consisting of 0.02 g of propolis ($R_w$=350/1) and 30 g of water is added at a temperature below about 70° C., with stirring. Stirring is continued until the mixture has cooled to RT, after which it is homogenized to give an ointment consisting of a water-in-oil emulsion, which can be used as an eye lotion.

EXAMPLE 4

Formulation 4.66 g of polyethylene glycol stearate 1500 are mixed with 13 g of glycerol monostearate, 3 g of glycerol monooleate, 10.5 g of decyl oleate, 5.5 g of capric/caprylic triglyceride and 5 g of glycerol isostearate. The mixture is heated gradually to 70–75° C. and heating is stopped as soon as the mixture has become homogeneous. 8 g of HGt4 are then added and the mixture is stirred slowly. 3 g of propylene glycol, 0.3 g of citral, 0.04 g of Prp ($R_w$=400/1) and 47 g of water are then poured into the resulting mixture. The mixture obtained is left to cool to RT, with stirring. It is then passed through a homogenizer to give a water-in-oil emulsion having the consistency of a cream.

EXAMPLES 5–12

Formulations

The following compositions, in which only the phenol component is mentioned and the weight ratio $R_w$=Cp/Prp is given in brackets, are obtained by the procedure indicated in Example 4, except that the phenol component HGt4 is replaced with an appropriate amount of another phenol.

Ex. 5: bisphenol A ($R_w$=250/1),
Ex. 6: pyrogallol ($R_w$=270/1),
Ex. 7: carvacrol ($R_w$=300/1),
Ex. 8: pyrocatechol ($R_w$=270/1),
Ex. 9: 2-(3,4-methylenedioxybenzyl)-4-t-butylphenol ($R_w$=340/1),
Ex. 10: 2-(3,4-dihydroxybenzyl)-4-(1,1,3,3-tetramethylbutyl) phenol ($R_w$=450/1),
Ex. 11: HGt8 ($R_w$=420/1),
Ex. 12: HGt5 ($R_w$=190/1).

EXAMPLE 13

Preparation of Purified Propolis

The propolis used in Examples 1–12 above is a purified propolis obtained by extraction with 80% EtOH (i.e. an EtOH/$H_2O$ mixture in a weight ratio of about 8/2), as indicated below.

The crude Prp is deposited by the bees on perforated plastic grids mounted on frames placed in the beehives. These grids, containing the crude Prp, are removed from the beehives and cooled to −30° C. in a freezer so as to make the crude Prp brittle, after which it is ground in a mortar. The ground material is extracted with 80% EtOH, at a rate of 1 part by weight of crude Prp to 10 parts by volume of 80% EtOH, for 24 h at RT, with stirring. The insoluble residue is filtered off. The filtrate collected is evaporated under reduced pressure to give a light brown dry extract. Yield: 65% by weight, based on the starting crude Prp.

What is claimed is:

1. An antiviral composition comprising a physiological acceptable carrier and an antiviral effective amount of a synergistic mixture consisting of
   (i) from 100 to 650 parts by weight of a phenol component and
   (ii) one part by weight of purified propolis.

2. A composition according to claim 1, wherein the phenol component is selected from the group consisting of phenol, pyrocatechol, resorcinol, hydroquinone, benzene-1,2,4-triol, pyrogallol, phloroglucinol, gallic acid, saligenol, vanillin, vanillyl alcohol, vanillic acid, vanillylmandelic acid, o-cresol, m-cresol, p-cresol, o-cresotic acid, m-cresotic acid, p-cresotic acid, guaiacol, eugenol, creosol, thymol, orcinol, p-anol, salicylic acid, chavicol, carvacrol, 4-t-butyl-phenol, butylparaben, benzoresorcinol bisphenol A, bisphenol B, bis(2-hydroxy-4-methoxyphenol) methanone, 1-naphthol, 2-naphthol, anthranol, anthrarobin, anthralin, anthrarufin and mixtures thereof.

3. A composition according to claim 1, wherein the phenol component is selected from the group consisting of
  (i) the 2,6-di-t-butylphenols of the formula

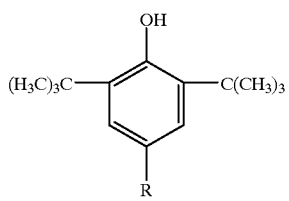

(I)

in which R is the hydrogen atom or a $C_1$–$C_{12}$ alkyl group with a linear or branched hydrocarbon chain, and
  (ii) mixtures thereof.

4. A composition according to claim 1, wherein the phenol component is selected from the group consisting of
  (i) the 2-benzylphenols of the formula

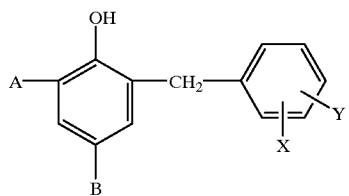

(II)

in which
X and Y independently of one another are each the hydrogen atom, a group OH, a group MeO or a group EtO, or X and Y, taken together, form a 3,4-methylenedioxy radical, A is H or a radical $CH_2C_6H_3XY$, in which X and Y are defined as indicated above, and
B is the hydrogen atom or a $C_1$–$C_{12}$ alkyl group with a linear or branched hydrocarbon chain, and
  (ii) mixtures thereof.

5. A composition according to claim 1, wherein the phenol component is selected from the group consisting of the following compounds:
  (a) 2,6-di-t-butylparacresol,
  (b) 2,4,6-tri-t-butylphenol,
  (c) 2,6-di-t-butyl-4-(2,2-dimethylpropyl)phenol,
  (d) 2,6-di-t-butyl-4-n-hexylphenol,
  (e) 2,6-di-t-butyl-4-(1,1,3,3-tetramethylbutyl) phenol
  (f) bisphenol A,
  (g) pyrogallol,
  (h) pyrocatechol,
  (i) carvacrol, and
  (j) mixtures thereof.

6. A composition according to claim 1, wherein the weight ratio phenol compound/propolis is between 135/1 and 560/1.

7. A method of treating lipid capsid viruses in an animal in need of such treatment which comprises administering to said animal an antiviral effective amount of a synergistic mixture consisting of (i) from 100 to 650 parts by weight of a phenol component, and (ii) one part by weight purified propolis.

8. The method of claim 1 in which the weight ratio of phenol component to propolis is between 135/1 and 560/1.

9. The method of claim 8 in which the viral disease is herpes simplex.

10. The method of claim 7 in которой the viral disease is herpes simplex.

11. Method according to claim 1, wherein the weight ratio phenol component/propolis is between 135/1 and 560/1.

* * * * *